United States Patent [19]

Nishino et al.

[11] Patent Number: 6,043,243
[45] Date of Patent: Mar. 28, 2000

[54] PYRROLIDINE DERIVATIVE, ANTI-ULCER DRUG, AND ANTIBACTERIAL DRUG

[75] Inventors: Chikao Nishino, Kanagawa; Tomohiro Uetake, Tokyo, both of Japan

[73] Assignee: Shiseido Co., Ltd., Tokyo, Japan

[21] Appl. No.: 09/204,273

[22] Filed: Dec. 3, 1998

Related U.S. Application Data

[62] Division of application No. 09/053,659, Apr. 2, 1998, Pat. No. 5,925,667.

[30] Foreign Application Priority Data

Apr. 4, 1997 [JP] Japan ................................. 9-102630

[51] Int. Cl.⁷ .................... A61K 31/53; C07D 401/00
[52] U.S. Cl. .................... 514/244; 514/244; 514/925; 514/926; 514/927; 546/268.1; 546/268.4
[58] Field of Search ..................... 546/336, 268.1, 546/268.4; 514/244, 927, 925, 926

[56] References Cited

U.S. PATENT DOCUMENTS

| | | | |
|---|---|---|---|
| 3,542,788 | 11/1970 | Chinu et al. | 260/294 |
| 4,089,960 | 5/1978 | Gosteli et al. | 424/266 |

FOREIGN PATENT DOCUMENTS

| | | | |
|---|---|---|---|
| 0 735 031 A1 | 10/1996 | European Pat. Off. | C07D 295/18 |
| 0 736 526 A1 | 10/1996 | European Pat. Off. | C07D 231/04 |
| 54-073780 | 6/1979 | Japan | C07D 403/12 |
| 56-095165 | 8/1981 | Japan | C07D 207/09 |
| 0735031A1 | 10/1996 | Japan | C07D 295/18 |
| 0736526A1 | 10/1996 | Japan | C07D 231/04 |

OTHER PUBLICATIONS

Schmidt, et al Chemical Abstracts, vol. 120, No. 11, Mar. 14, 1994, Columbus, Ohio.
Desai, et al Chemical Abstracts, vol. 122, No. 5 46178e, Jan. 30, 1995, Columbus, Ohio.
Orzalesi, et al Chemical Abstracts, vol. 85, No. 23. Dec. 6, 1976, Columbus, Ohio.
LaBarre Chemical Abstracts, vol. 72, No. 1 Jan. 5, 1970, Columbus, Ohio.
D.E. Schmidt et al., Chemical Abstract, vol. 120, No. 11 Aromatic and amine substituent effects on the apparent lipophilieities of N-{2-pyrolidinyl}-substituted benzamides, Mar. 14, 1994.
J.K. Desai et al., Chemical Abstract, vol. 122, No. 5 Gastric and duodenal anti–ulcer activity of sulpiride, a dopamine, Jan. 30, 1995.
G. Orzalesi et al., Chemical Abstract, vol. 85, No. 23 Some new derivatives of 2–aminomethyl–N–ethylpyrrolidine 3–amino–N–ethylpiperidine with antiemetic and antiulcer activity Dec. 6, 1976.
J. LaBarre: Chemical Abstract, vol. 72, No. 1 Antigastric ulcer and excitomotor effects of sulpiride, Jan. 5, 1970.

*Primary Examiner*—S. Mark Clardy
*Assistant Examiner*—Sabiha N. Qazi
*Attorney, Agent, or Firm*—Snider & Associates; Ronald R. Snider

[57] ABSTRACT

A pyrrolidine derivative or a salt thereof expressed by the following formula 1:

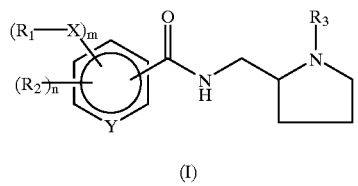

formula 1

(I)

wherein $R_1$ is an alkenyl group;

$R_2$ is a lower alkoxy group or a halogen atom;

$R_3$ is a lower alkyl group;

X is a group expressed by —O— or —S—;

Y is carbon or nitrogen atom;

m is an integer of 1 to 3; and n is an integer of 0 to 2.

The pyrrolidine derivative has an anti-ulcer effect or an antibacterial activity against *Helicobacter pyroli*, and has also high safety to be available for prevention or cure of ulcers.

16 Claims, 1 Drawing Sheet

Reaction formula A;

Reaction formula B;

Reaction formula C;

PYRROLIDINE DERIVATIVE, ANTI-ULCER DRUG, AND ANTIBACTERIAL DRUG

RELATED APPLICATIONS

This application is a divisional application of U.S. patent application Ser. No. 09/053,659 (filed on Apr. 2, 1998), which is U.S. Pat. No. 5,925,667 claims the priority of Japanese Patent Application No. 9-102630 filed on Apr. 4, 1997, which is incorporated herein by reference.

FIELD OF THE INVENTION

The present invention relates to a pyrrolidine derivative and, in particular, to a pyrrolidine derivative having an antibacterial activity against *Helicobacter pyroli* or an anti-ulcer effect.

BACKGROUND OF THE INVENTION

Various theories have been proposed with respect to a cause of ulcer in human. In particular, it has been elucidated that stress, taking of non-steroidal anti-inflammatory drugs for curing rheumatic diseases, and the like are closely related to ulcer formation, mainly due to relatively excess gastric or duodenal acid secretion. Accordingly, it is important to suppress the acid secretion in order to prevent ulcer formation and to cure it.

On the other hand, it has been considered that *Helicobacter pyroli*, which is a rod normally existing in stomach, generates ammonia due to its strong urease activity, thereby inducing ulcer. Since it persistently lives within mucus and mucosa, it becomes the greatest cause for recurrence of ulcer. Accordingly, it has been considered that the recurrence of ulcer can be prevented if this bacterium is sterilized.

Though various kinds of medicaments for curing ulcer have been conventionally developed, few medicaments have been known to have an effect for preventing stress ulcers from generating or an antibacterial activity against *Helicobacter pyroli*.

DISCLOSURE OF THE INVENTION

The present invention has been performed in view of the problems of the above-mentioned prior art and its object is to provide a compound which is excellent in preventing ulcer from generating and to provide antibacterial drug against *Helicobacter pyroli* and anti-ulcer drug including such a compound as a main component.

As a result of the diligent studies conducted by the inventors for the object, it has been found that a specific pyrrolidine derivative is effective against various kinds of ulcer due to its antibacterial property against *Helicobacter pyroli* or its acid secretion inhibition as a main action mechanism. Thus, the present invention has been accomplished.

Namely, a pyrrolidine derivative or a salt thereof in accordance with the present invention is expressed by the following formula 1:

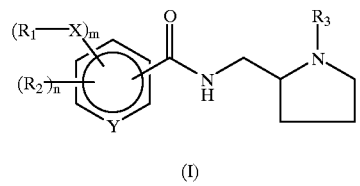

formula 1

(I)

wherein $R_1$ is an alkenyl group;
$R_2$ is a lower alkoxy group or a halogen atom;
$R_3$ is a lower alkyl group;
X is a group expressed by —O— or —S—;
Y is carbon or nitrogen atom;
m is an integer of 1 to 3; and
n is an integer of 0 to 2.

An anti-ulcer drug in accordance with the present invention comprises, as an effective ingredient, said pyrrolidine derivative or the pharmacologically acceptable salt thereof, together with a pharmaceutically acceptable carrier and/or adjuvant.

An antibacterial drug against *Helicobacter pyroli* in accordance with the present invention comprises, as an effective ingredient, said pyrrolidine derivative or the pharmacologically acceptable salt thereof, together with a pharmaceutically acceptable carrier and/or adjuvant.

A method for the treatment of peptic ulcers in man or mammals in accordance with the present invention comprises administering an effective amount of said pyrrolidine derivative or the pharmacologically acceptable salt thereof to a host.

A method for the inhibition of acid secretion in stomach of man or mammals in accordance with the present invention comprises administering an effective amount of said pyrrolidine derivative or the pharmacologically acceptable salt thereof to a host.

A method for the inhibition of growth of *Helicobacter pyroli* in stomach of man or mammals in accordance with the present invention comprises administering an effective amount of said pyrrolidine derivative or the pharmacologically acceptable salt thereof to a host.

A method for the prevention of peptic ulcers in man or mammals in accordance with the present invention comprises administering an effective amount of said pyrrolidine derivative or the pharmacologically acceptable salt thereof to a host.

EXAMPLES

In the compound of the present invention, the alkenyl group found at $R_1$ represents a straight or branched alkenyl group which has at least one double bond and has 2 to 20 carbon atoms. While the double bond has two kinds of configurations, namely, cis and trans, each double bond in alkenyl group may have either configurations. Among them, it is preferably a branched alkenyl group and, particularly preferable examples of alkenyl group are prenyl, geranyl, neryl and farnesyl group.

In the compound of the present invention, $R_2$ represents a lower alkoxy group or a halogen atom. Such a lower alkoxy group represents that derived from a lower alkyl group of $R_3$ mentioned below. A preferable example of lower alkoxy group is methoxy group. Examples of halogen atom include fluorine, chlorine, bromine, and iodine. A preferable example of halogen is fluorine.

The lower alkyl group found at $R_3$ is a straight or branched alkyl group having 1 to 6 carbon atoms. Examples thereof include methyl, ethyl, n-propyl, n-butyl, isopropyl, isobutyl, 1- methylpropyl, tert-butyl, n-pentyl, 1-ethylpropyl, isoamyl, and n-hexyl group. A preferable example of $R_3$ is ethyl group.

In the compound of the present invention, X represents a group shown by —O— or —S—. A preferable example of X is —O—.

A preferable compound of the present invention may be expressed by the following formula 2:

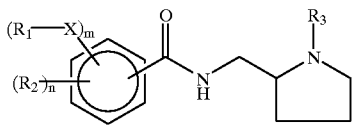

formula 2 wherein $R_1$, $R_2$, $R_3$, X, m and n are same as those in the above-mentioned formula 1.

In the formula 1 or 2, it is preferable that n is 0.

Also, in the formula 1 or 2, it is preferable that n is 1 or 2. Further, it is preferable that m is 1 when n is 1 or 2.

In the formula 1 or 2, it is preferable that X is —O—.

A preferable compound of the present invention may be expressed by the following formula 3:

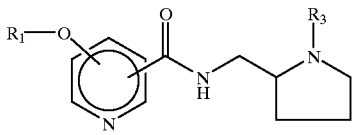

formula 3 wherein $R_1$ and $R_3$ are same as those in the above-mentioned formula 1.

In formula 3, it is preferable that carbon of the amide group bonds to 3- position of pyridine ring.

In the compound of the present invention, it is preferable that $R_1$ is prenyl, geranyl, neryl or farnesyl group.

In the compound of the present invention, it is preferable that $R_3$ is ethyl group.

In the following, while the general method for manufacturing the compound of the present invention will be explained, it should not be restricted thereto.

Figure 1:
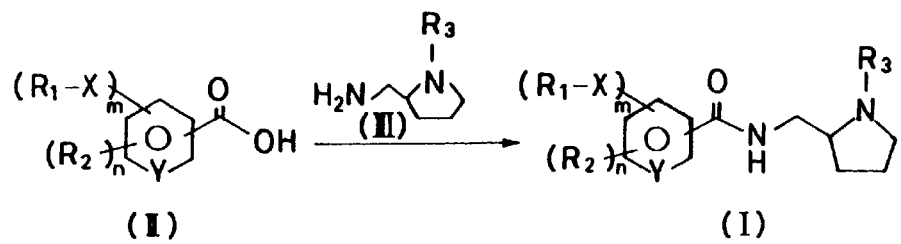
FIG. 1 shows an example of a step for manufacturing the pyrrolidine derivative in accordance with the present invention and FIGS. 2 and 3 show examples of steps for manufacturing material compounds for the pyrrolidine derivative in accordance with the present invention.

The compound(I) of the present invention expressed by formula 1 can be manufactured by reaction formula A shown in FIG. 1.

In reaction formula A, the pyrrolidine derivative(I) of the present invention can be obtained from a carboxylic acid(II) and an amine(III) by using a known amide-bond forming reaction such as mixed anhydride method, acid chloride method, DCC method, CDI method, or azide method. Here, in reaction formula A, $R_1$, $R_2$, $R_3$, X, Y, m and n are defined as those of formula 1 mentioned above.

In the mixed anhydride method, by using an activator such as diphenyl phosphinic chloride, ethyl chloroformate, isobutyl chloroformate, or pivaloyl chloride, the carboxylic acid (II) is converted into its corresponding anhydride and then reacted with the amine(III). As an additive, for example, an organic base such as triethyl amine, pyridine, or N-methylmorpholine can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of −15° C. to the reflux temperature of the solvent.

In the acid chloride method, as an activator, for example, phosphorus pentachloride, phosphorus trichloride, or thionyl chloride is used to convert the carboxylic acid (II) into the corresponding acid chloride and then the latter is reacted with the amine (III). As an additive, for example, an organic base such as triethyl amine, pyridine, or N-methylmorpholine can be used. As a solvent, for example, a halogenated hydrocarbon such as dichloromethane or chloroform; an aromatic hydrocarbon such as benzene, toluene, or xylene; or an amide such as dimethyl formamide or dimethylacetamide can be used. While the reaction temperature and reaction time may be changed according to the material compounds used, the reaction is usually effected at a temperature within the range of 0° C. to the reflux temperature of the solvent.

In the DCC method, as a condensing agent, for example, dicyclohexyl carbodiimide (DCC) or 1-ethyl-3-(3-dimethylaminopropyl)carbodiimide hydrochloride (WSCI) can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. If necessary, this reaction may be effected while 1-hydroxybenzotriazole (HOBt) or N-hydroxy succinimide (HOSu) is added thereto. While the reaction temperature and reaction time may be changed according to the material compounds used, the reaction is usually effected at a temperature within the range of 0° C. to the reflux temperature of the solvent.

In the CDI method, as an activator, for example, N,N'-carbonyldiimidazole is used to convert the carboxylic acid (II) into the corresponding N-acyl derivative and then the latter is reacted with the amine(III). As an additive, for example, an organic base such as triethylamine, pyridine, or N-methylmorpholine or an inorganic base such as sodium hydride or potassium hydride can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of 0° C. to the reflux temperature of the solvent.

In the azide method, as an activator, for example, diphenylphosphorylazide is used to convert the carboxylic acid (II) into the corresponding azide and then the latter is reacted with the amine (III). As an additive, for example, an organic base such as triethylamine, pyridine, or N-methylmorpholine is used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of 0° C. to the reflux temperature of the solvent.

Specifically, for example, diphenylphosphinic chloride or pivaloyl chloride is used as an activator for the mixed anhydride method, while triethylamine is used as an additive to effect a reaction in a solvent such as chloroform or dimethyl formamide at a temperature within the range of −15° C. to room temperature, thereby attaining the aimed object.

Figure 2:
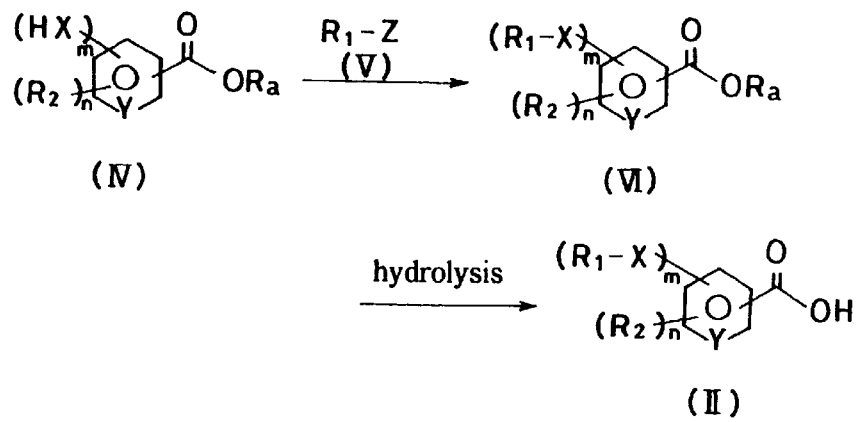

The material compound(II) used in reaction formula A can be synthesized by reaction formula B shown in FIG. 2, for example. In reaction formula B, $R_1$, $R_2$, X, Y, m, and n are defined as those of formula 1 mentioned above. Ra represents a carboxyl-protecting group which may be a lower alkyl group such as methyl group, ethyl group, or tert-butyl group, phenacyl group, or trichloroethyl group as long as no problem occurs in the subsequent reaction. Z represents a halogen atom.

In reaction formula B, an alkenyl halide(V) is reacted with a compound(IV) in the presence of a base and then hydrolyzed so as to synthesize the carboxylic acid (II).

The first step of this reaction can be effected in the presence of a base. Sodium amide, triethylamine, sodium hydride, sodium hydroxide, potassium carbonate, barium oxide, silver oxide, or the like can be used therefor. Also, a catalytic amount of potassium iodide can be added thereto. As a solvent, for example, an alcohol such as methanol, ethanol, or butanol; an aromatic compound such as benzene, toluene, xylene, or pyridine; an ether such as diethylether, tetrahydrofuran, or dioxane; an amide such as dimethylformamide or dimethylacetamide; or a ketone such as dimethylsulfoxide or acetone can be used. While the reaction temperature and reaction time may be changed according to the material compounds used, the reaction is usually effected at a temperature within the range of 0° C. to the reflux temperature of the solvent.

Specifically, for example, the compound (IV) is dissolved in tetrahydrofuran or N,N'-dimethylformamide and, after sodium hydride is added as a base and stirred therein, the alkenyl halide(V) is added thereto so as to effect a reaction at a temperature within the range of room temperature to the reflux temperature of the solvent, thereby attaining the aimed object.

In the reaction of the second step, the ester compound (VI) is hydrolyzed in the presence of an acid or a base so as to synthesize the carboxylic acid (II). Hydrochloric acid, sulfuric acid, p-toluenesulfonic acid, or the like can be used as the acid, while sodium hydroxide, potassium hydroxide, potassium t-butoxide, or the like can be used as a base. As a solvent, a carboxylic acid such as formic acid or acetic acid; an alcohol such as methanol or ethanol; water; or a mixed solvent thereof can be used. While the reaction temperature and reaction time can be changed according to the material compounds used, the reaction is usually effected at a temperature within the range of 0° C. to the reflux temperature of the solvent.

Specifically, for example, the ester compound(VI) is dissolved in an alcohol such as methanol or ethanol and then an aqueous sodium hydroxide or potassium hydroxide solution is added thereto so as to effect a reaction at a temperature within the range of room temperature to reflux temperature of the solvent, thereby attaining the aimed object.

Figure 3:

The material compound (V) used in reaction formula B can be synthesized by reaction formula C shown in FIG. 3.

In reaction formula C, $R_1$ and Z are defined as those of reaction formula B mentioned above. In this reaction, an alkenyl halide (V) can be obtained by halogenation of alcohol (VII).

For this reaction, a general method known as halogenation of hydroxy groups can be used. As a reagent of halogenation, for example, a strong acid such as hydrochloric acid or hydrobromic acid; a phosphorus compound such as phosphorus tribromide, phosphorus trichloride, or phosphorus pentachloride; thionyl chloride; N-halogenosuccinimide and dimethyl sulfide; triphenylphosphine and a halogenated hydrocarbon; or methanesulfonyl chloride and lithium halide is used to effect the reaction. As a solvent, for example, a halogenated hydrocarbon such as dichloromethane or chloroform; an aromatic compound such as benzene, toluene, xylene, or pyridine; an ether such as diethylether, tetrahydrofuran or dioxane; or an amide such as N,N-dimethylformamide or N,N-dimethylacetamide can be used. While the reaction temperature and reaction time may be changed according to the material compounds used, the reaction is usually effected at a temperature within the range of 0° C. to the reflux temperature of the solvent.

Specifically, for example, in the presence of lithium chloride and triethylamine, methanesulfonyl chloride is used so as to effect a reaction in a solvent such as acetone at a temperature within the range of 0° C. to room temperature, thereby attaining the aimed object.

Among the material compounds used in the above-mentioned reaction formulas, those with no preparation methods described may be commercially available or easily synthesized by using a known method.

Also, examples of salts of the pyrrolidine derivative(I) of the present invention with an acid include salts with inorganic acids such as hydrochloric acid, hydrobromic acid, sulfuric acid, or phosphoric acid and salts with organic acids such as acetic acid, propionic acid, citric acid, lactic acid, oxalic acid, maleic acid, fumaric acid, succinic acid, tartaric acid, or methane sulfonic acid. These salts can be easily manufactured by a normal method.

The pyrrolidine derivative in accordance with the present invention has a strong effect against stress ulcer and an excellent effect for suppressing gastric acid secretion. Further, it has an antibacterial activity against *Helicobacter pyroli* which is supposed to be a cause for recurrence of ulcer. Furthermore, it has a high safety. Accordingly, it is useful as a medicament for curing and preventing peptic ulcer in man or mammals and, particularly, gastric ulcer in man. Conventionally, there has hardly been known such a compound which has both effect for suppressing gastric acid secretion and antibacterial activity against *Helicobacter pyroli*. Accordingly, it is indicated that the compound of the present invention is not only effective in preventing and curing ulcer but also in preventing the recurrence thereof.

When the compound of the present invention is administered as a medicament for curing and preventing peptic ulcer, it may be administered orally as tablet, powder, granule, capsule, syrup, or the like as well as parenterally as suppository, injection, external drug, instillation or the like. While the amount of administration may be outside of the range mentioned below according to the degree of symptom, personal difference, age, kind of ulcer, or the like, it should of course be adjusted so as to fit the individual circumstances in specific cases. Usually 0.01 to 200 mg/kg or, preferably, 0.05 to 50 mg/kg or, more preferably, 0.1 to 10 mg/kg is administered per day for an adult in a single dose or several doses.

When formulating the medicament, a normal manufacturing method is used with a normal formulation carrier. If necessary, pharmacologically and pharmaceutically acceptable additives may be added thereto.

Namely, when preparing an oral solid formation, after an excipient and, if necessary, a binder, a decaying agent, a luster, a coloring agent, a correctives, and the like are added to the main medicament, a normal method is used to form tablet, coated tablet, granule, powder, capsule, or the like.

Examples of the excipient include lactose, corn starch, sucrose, glucose, sorbitol, crystalline cellulose, and silicon dioxide. Examples of the binder include polyvinylalcohol, polyvinylether, ethyl cellulose, methyl cellulose, gum arabic, tragacanth, gelatin, shellac, hydroxypropyl cellulose, hydroxypropyl starch, and polyvinylpyrrolidone. Examples of the decaying agent include starch, agar, gelatin powder, crystalline cellulose, calcium carbonate, sodium hydrogencarbonate, calcium citrate, dextrin, and pectin. Examples of the luster include magnesium stearate, talc, polyethyleneglycol, silica, and hardened vegetable oil. As the coloring agent, those permitted to be added to medicines are used. Examples of the correctives include cocoa powder, menthol, aromatic acid, mentha oil, borneol, and cinnamon powder. If necessary, these tablet and granule can be coated with sugar-coating, gelatin-coating, and the like.

When preparing an injection, if necessary, a pH-adjusting agent, a buffer, a stabilizer, a solubilizer, and the like are added to the main medicament and then a normal method is used to form subcutaneous, intramuscular, and intravenous injection drugs.

In the following, the present invention will be explained in further detail by specifically examples. However, the present invention should not be restricted to these examples.

First, test methods used for evaluating these examples will be explained.

WIS: Restraint and Water Immersion Stress-Induced Ulcer Inhibition Test i)Meaning The degree of inhibition of the stress ulcer formation is tested.

ii)Method

Male Crj:SD or Slc:SD rats (6 to 7-week-old) were fasted overnight, but allowed free access to water. Each group has 5 to 8 of these rats. The sample compound was dissolved or suspended in an aqueous solution of 0.3% sodium carboxymethylcellulose or 0.05% Tween 80 and then was orally administered (100 mg/10 ml/kg). To a control group, the vehicle was administered. 10 minutes later, the rats were placed in a stress cage and immersed to the level of xipfoid process in a water bath (21° C.) for 7 hours. At the end of the stress, the rats were sacrificed by inhalation of ether or carbon dioxide. Then, the stomach of each was removed, inflated by injecting 10 ml of 5% formalin neutral buffer solution, and immersed in 1% formalin neutral buffer solution for 30 minutes or more to be fixed. The stomach was incised along the greater curvature and then the length of each erosion in the glandular portion was determined under dissecting microscope. The sum of the length of erosions per stomach was defined as ulcer index (UI).

iii)Judgment Standard

The effect obtained when 100 mg/kg of the sample compound had been administered was expressed as ulcer formation inhibitory rate (%) as follows:

ulcer formation inhibitory rate (%)=(1-(UI in sample group/UI in control group))×100

CAP: Acid Secretion Inhibition Test In Vitro i)Meaning

The acid secretion inhibitory activity in a cell level is studied. It can also be used for studying the mechanism of the effect.

ii)Method ii-a) Preparation of isolated gastric fundus gland suspension

First, an isolated gastric fundic gland sample was prepared. Namely, a male Japanese White rabbit (2.5 to 3 kg) was anesthetized to death with Nembutal™ and then the abdomen was incised. Immediately thereafter, the stomach was removed and, after pyloric and cardiac antrum were severed, incised along its greater curvature into two sheets. The gastric contents adhering to the mucosal surface was washed out with ice-cooled PBS (−) and then carefully washed therein. The gastric wall was spread on a cork board with its mucosal surface facing up and the feed and mucus thereon were completely removed with sterile gauze. The mucosa was separated therefrom by a spatula and then collected in ice-cooled PBS (−). After being washed twice with PBS (−), the mucosa was minced into 2–3 mm$^3$ pieces by scissors. These pieces were further washed twice with a nutrient solution. The nutrient solution comprises 132.4 mM of NaCl, 5.4 mM of KCl, 5 mM of $Na_2HPO_4 \cdot 12H_2O$, 1 mM of $NaH_2PO_4 \cdot 2H_2O$, 1.2 mM of $MgSO_4$, 1 mM of $CaCl_2$, 25 mM of HEPES, 2 mg/ml of glucose, and 1 mg/ml of BSA.

Into 70 ml of the nutrient solution containing 1 mg/ml of collagenase, minced mucosal pieces were dispersed and intensely stirred in a conical flask with a stirrer at 37° C. for 40 to 60 minutes. During this period, 100% 02 was sprayed on the nutrient solution surface and the pH was appropriately measured such that it was immediately adjusted to pH 7.4, when the value was therebelow, with a base. The nutrient solution was added to the reaction solution so as to attain the total amount of about 200 ml. After being filtered through a mesh, the suspension was divisionally introduced into 50 ml centrifuge tubes and left for 15 minutes such that gastric fundic gland was deposited. The supernatant was repeatedly removed by an aspirator, dispersed in the nutrient solution, and then left such that the gastric fundic gland was washed three times. At this time, without using a pipette, the suspension was alternately introduced into two centrifuge tubes so as to effect dispersion. The number of cells was counted under microscope and adjusted to $1.6 \times 10^6$ cells/ml.

ii-b) [$^{14}$C]-aminopyrine uptake test

Then, [$^{14}$C]-aminopyrine uptake test was performed. After an Eppendorf tube was weighed, 10 µl (final concentration: $10^{-5}$M) of histamine dissolved in the above-mentioned nutrient solution, 10 µl (final concentration: $10^{-5}$M) of the test compound dissolved in DMSO, and 10 µl (final concentration: 0.05 µCi/ml) of [$^{14}$C]-amino/pyrine diluted with the nutrient solution were introduced therein and then 970 µl of the isolated gastric fundic gland suspension prepared above was added thereto. Subsequently, this mixture was shaken at 37° C. for 40 minutes at 125 cycles/minute. After being centrifuged for 30 seconds, 200 µl of its supernatant was collected into a mini-vial, while the rest was removed by an aspirator. The gland pellet was completely dried as the tube with its lid being opened was kept for one night in a drying oven at 80° C. and then the lid was closed and the weight was determined at room temperature. Then 100 µl of 1N KOH was added thereto and the tube with its lid being closed was treated at 60° C. for 1 to 2 hours so as to dissolve the pellet. Then, the contents thereof were transferred to a mini-vial. Into the mini-vial containing the supernatant or gland pellet, 4 ml of Atomlite™ was added and then the radioactivity was measured by a liquid scintillation counter. Here, after the radioactivity of the gland pellet was corrected by using a sample in which 20 mM of NaSCN was added so as to cancel the hydrogen ion concentration gradient, the integration ratio of aminopyrine specifically trapped by the gland pellet was calculated. This experiment was performed in duplicate.

ii-c) Calculation of the accumulation rate of aminopyrine

Here, its principle will be briefly explained. In the isolated gastric fundic gland, acid is accumulated in a space between its secretory tubule and intraglandular cavity. Aminopyrine is weak base (pKa=5.0) and nonionic in a neutral solution so as to freely pass through the cell membrane, whereas it is ionized in an acidic solution and thus cannot pass through the cell membrane due to its electric charge. Therefore, aminopyrine is accumulated in a closed acidic space within the isolated gastric fundic gland. In view of this characteristic, the accumulation rate (R) of aminopyrine is calculated by the following equation:

R=((corrected radioactivity of precipitate)/(radioactivity of supernatant))×(200/(mg dry weight of gland pellet))

iii)Judgment Standard

The effect of the sample compound at the final concentration of $10^{-5}$M was expressed by acid secretion inhibitory rate (%) as follows:

acid secretion inhibitory rate (%)=(1-(R in sample group/R in control group))×100

AHP: Antibacterial Activity Test Against *Helicobacter pyroli* i)Meaning

The minimum inhibitory concentration (MIC) against *Helicobacter pyroli* (microaerophilic gram-negative bacterium which is supposed to deeply involve in pathogenesis, relapse, and recrudescence of ulcer, referred to as "HP" in the following) is measured so as to find out compounds which have antibacterial activity against *Helicobacter pyroli*.

ii)Method

MICs were determined by the agar dilution method. The stock culture (-80° C.) of HP NCTC 11637 was thawed and cultured on tripticase soy agar supplemented with 5% sheep blood at 37° C. in an atmosphere of 5% $O_2$, 10% $CO_2$, and 85%$N_2$. Grown colonies were transferred to the same plate and precultured for 3 days under the same condition.

A 1,000 µg/ml solution of the sample compound containing DMSO not more than 25% was diluted with sterile purified water so as to have various kind of concentrations. 100 µl volume from each dilution was mixed thoroughly with 900 µl of brucella agar supplemented with 5% horse blood and solidified in a 24 well micro plate, thereby yielding an MIC measurement plate.

An appropriate amount of the colony grown on the plate by preculturing was suspended in Mueller Hinton broth till turbidity was recognizable by naked eyes, thereby yielding a bacterial suspension concentrate containing about 107 cfu/ml. This bacterial suspension concentrate was diluted 100-fold in the same broth; this resulted in a bacterial suspension for inoculation containing about $10^5$ cfu/ml of the bacteria.

10 µl of the bacterial suspension for inoculation (about $10^3$ cfu) was dropped dispenser onto an MIC plate for inoculation and cultured fair 7 days under the same condition as that of preculture. Thereafter, it was judged whether there had been bacteria growth or not.

iii)Judgment Standard

The minimum concentration of the sample compound when there were no visible colonies or, if any, 5 or less colonies of HP was defined as MIC (µg/ml).

AT: Single Dose Toxicity Pretest i)Method

Male Slc:ICR mice (5-week-old) were used. Each group has 3 to 5 mice and each mouse was fasted, but allowed free access to water, for 4 to 5 hours from 9 a.m. in the test day. Then, 2,000 mg/10 ml/kg of the sample compound dissolved or suspended in an aqueous solution of 0.5% sodium carboxymethyl cellulose was orally administered thereto. To a control, only the vehicle was administered. The behavior and symptom were observed at each of 15 minutes, 30 minutes, 1 hour, 2 hours, and 3 hours after the administration and then daily till one week thereafter. The body weight was measured before and after the fasting as well as at the same time everyday. The dead animals were immediately subjected to autopsy and their organs were observed by naked eyes. Also, the living animals were sacrificed with ether or carbon dioxide one week after the administration and then their organs were observed by naked eyes.

ii)Judgment Standard

The toxicity at the single dose of 2,000 mg/kg of the sample compound was expressed as being classified into 5 levels.

5: Mortality rate is 0%; no toxicity is found at all both in behavior and organs.

4: Mortality rate is 0%; while no toxicity is found in organs, slight toxicity is observed in behavior or body weight increase.

3: While there is a dead animal (though not all the animals are dead), no toxicity is found in organs.

2: Regardless of whether there is a dead animal or not, toxicity is found in organs.

1: All the animals are dead.

MTT: Cell Damaging and Protecting Effect Test i) Meaning

It is confirmed that there is no toxicity in cell level. Those having a toxicity in cell level are inappropriate as an anti-ulcer drug. Also, it can be confirmed that the effects of the sample compounds in other cell level tests do not result from their toxicity.

ii) Method

A male Japanese White rabbit (2.5 to 3 kg) was anesthetized to death by Nembutal™ and, immediately thereafter, its stomach was removed. The greater curvature of the stomach was incised so as to remove the stomach contents therefrom. After the mucosal surface was washed with HBSS (Hanks' Balanced Salt Solution), the stomach in ice-cooled HBSS was transferred to a laboratory. Then, after the pyloric antrum was removed, the gastric corpus mucosa was separated by a spatula and then minced into 2 to 3 mm$^3$ pieces in BME (Basal Medium Eagle). Thereafter, these pieces were shaken at 120 to 130 cycles/minute for 15 minutes at 37° C. in BME 60ml containing 280 U/ml of dispase and 30 to 50 U/ml of collagenase. Here, the concentration of collagenase was appropriately changed for each lot in view of the state of cells. The pieces were washed twice with EBSS (Earle's Balanced Salt Solution) containing 1 mM of EDTA and then shaken in MEM (Minimum Essential Medium) containing 1 mM of EDTA at 37° C. for 5 minutes. Subsequently, they were shaken in the dispase and collagenase having the same concentrations as those mentioned above for 15 minutes so as to remove the supernatant and then further shaken at 37° C. for 50 to 60 minutes at 120 to 130 cycles/minute. Then, after being washed twice with HBSS, Ham F12 containing 2% of Ultrocer G™ was used to attain the concentration of $1\times10^6$ cells/ml. Thus formed suspension was dispensed in each well of a 96-well plate by 200 μl. The plate was incubated in the atmosphere composed of 5% $CO_2$ and 95% air at 37° C. for three days so as to attain a confluent state and then subjected to MTT assay.

The sample compound was dissolved in DMSO so as to attain a concentration of $10^{-2}$M and then diluted with HBSS containing 2% of Ultrocer G™ so as to attain a final concentration of $10^{-4}$M. To each group, which 8 wells were used for, 10 μl of MTT reagent was added immediately after 100 μl of the medium in each well was exchanged for same volume of the resulting solution of the sample compound. After being incubated in an atmosphere composed of 5% $CO_2$ and 95% air at 37° C. for 4 hours, thus formed solution was centrifuged and then its supernatant was discarded. Subsequently, 100 μl of 100% ethanol was added to the residue so as to dissolve MTT formazan. Then, the absorbance (OD: 570 to 630) was measured by a microplate reader. This method utilizes a phenomenon in which MTT is changed to MTT formazan only by mitochondria of living cells so as to change color.

iii) Judgment Standard

The cell damaging or cell protecting effect of the sample compound at the final concentration of $10^{-4}$M was expressed as cell damaging rate (%) as follows:

cell damaging rate (%)=(1-(absorbance in sample group/absorbance in control group))×100

Accordingly, the smaller value is better in the cell damaging rate.

Based on the foregoing effect tests and safety tests, example compounds of the present invention were tested.

Compound Group 1

A pyrrolidine derivative of this compound group 1 is a compound in which n is 0 among compounds corresponding to formula 2 mentioned above. As the pyrrolidine derivatives of this compound group 1, the following compounds were tested.

Example 1:

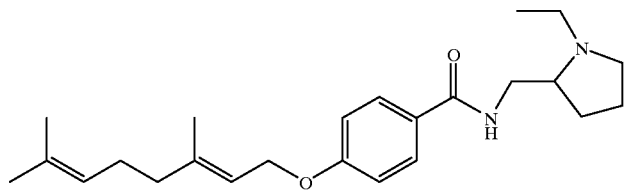

Example 2:

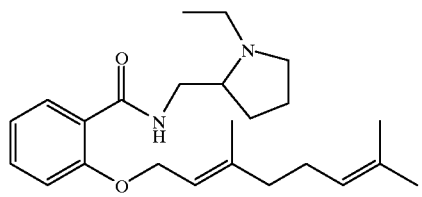

-continued
Example 3:
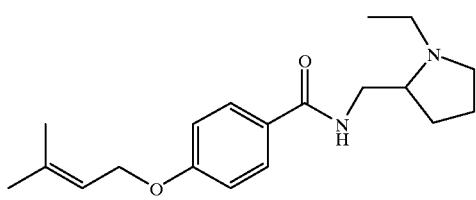
Example 4:
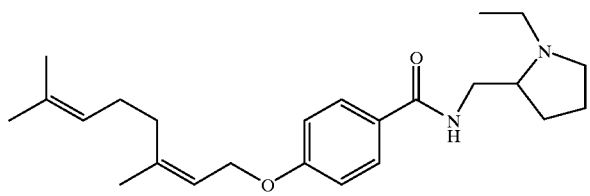
Example 5:
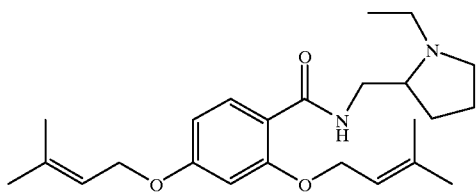
Example 6:
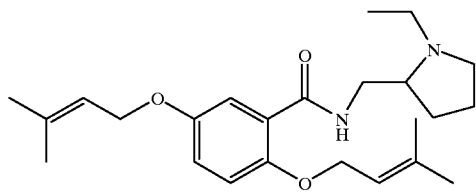
Example 7:
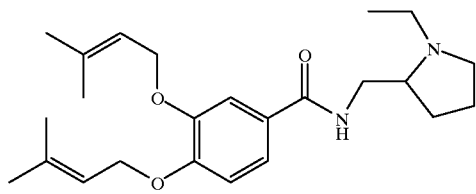
Example 8:
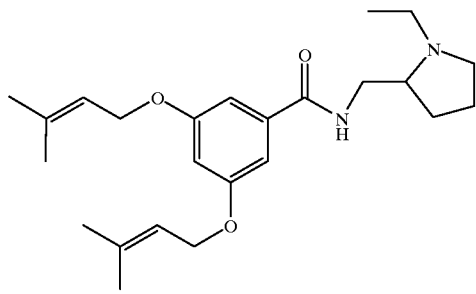
Example 9:
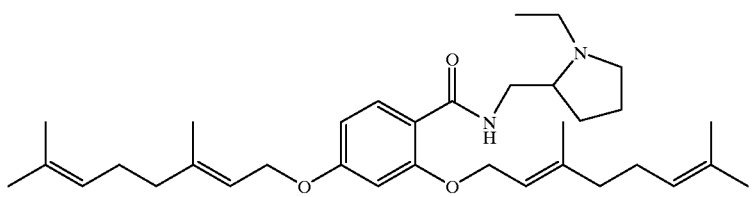

-continued

Example 10:

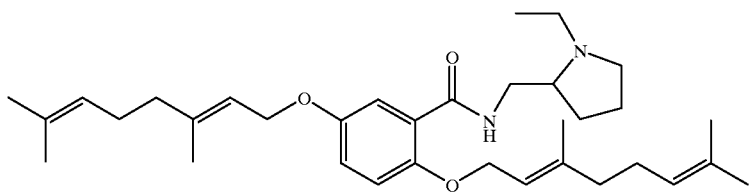

Example 11:

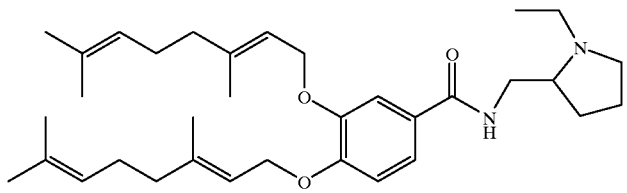

Example 12:

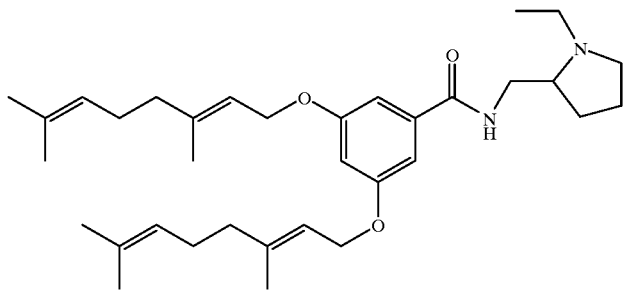

Example 13:

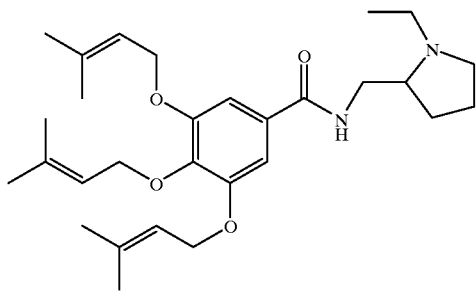

Example 14:

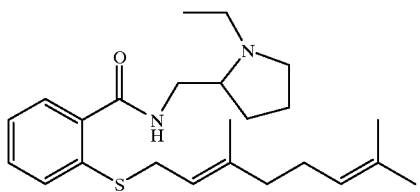

As clearly from Table 1, a compound of this compound group 1 has an excellent anti-ulcer effect and acid secretion inhibition effect and there is a compound having an anti-bacterial activity against *Helicobacter pyroli* together with. Also, it can be understood that they have high safety.

Here, in this compound group 1, though X is preferably —O—, even when X is —S— such as Example 14, the effect has been maintained.

TABLE 1

| Example No. | Anti-ulcer Tests | | Anti-HP Test | Tests for Safety | |
|---|---|---|---|---|---|
| | WIS | CAP | AHP | MTT | AT |
| 1 | 80 | | | | |
| 2 | 85 | 99.7 | | 19 | |
| 3 | 86 | 61.0 | | −14 | |
| 4 | 68 | 100.3 | | | 5 |
| 5 | 70 | 100.1 | | 9 | |
| 6 | 84 | 100.2 | | 34 | 3 |
| 7 | 92 | 99.7 | | 28 | 3 |
| 8 | 81 | 100.3 | | | 5 |

TABLE 1-continued

| Example No. | Anti-ulcer Tests | | Anti-HP Test | Tests for Safety | |
|---|---|---|---|---|---|
| | WIS | CAP | AHP | MTT | AT |
| 9 | 66 | | | | |
| 10 | 74 | 100.5 | <3.13 | 15 | 3 |
| 11 | 75 | | | | |
| 12 | 82 | 100.4 | | 29 | |
| 13 | 57 | | | | |
| 14 | 81 | 98.1 | | 27 | |

Compound Group 2

A pyrrolidine derivative of this compound group 2 is a compound in which n is 1 or 2 among compounds corresponding to formula 2 mentioned above. As the pyrrolidine derivatives of this compound group 2, the following compounds of Example 15 to 24 were tested.

Example 15:

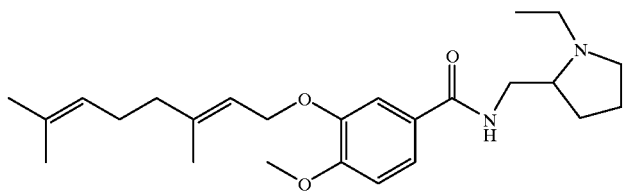

Example 16:

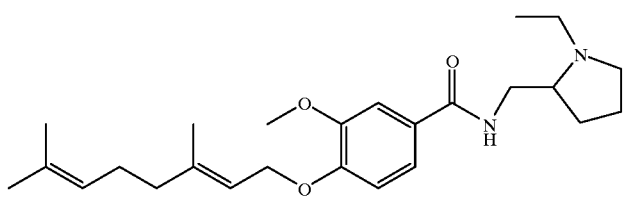

Example 17:

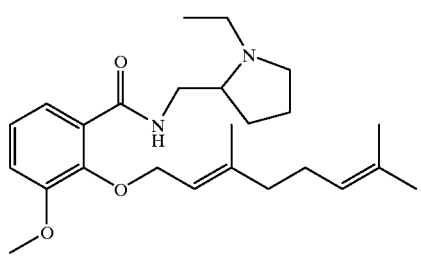

Example 18:

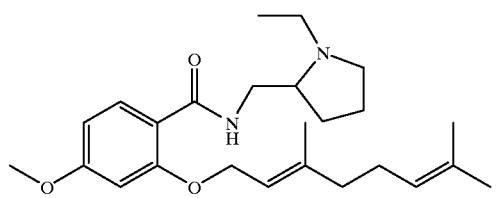

Example 19:

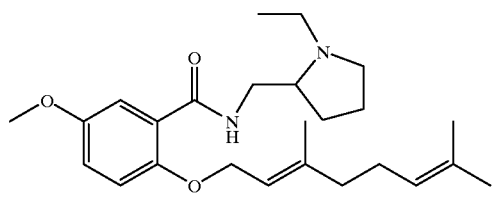

Example 20:
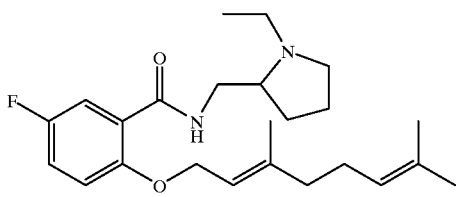
Example 21:
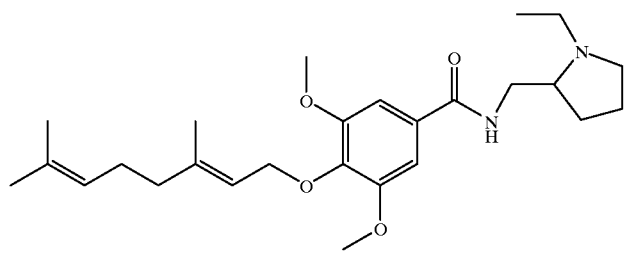
Example 22:
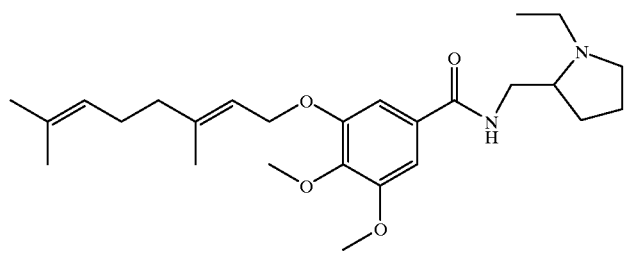
Example 23:
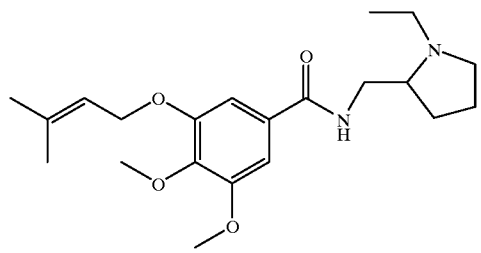
Example 24:
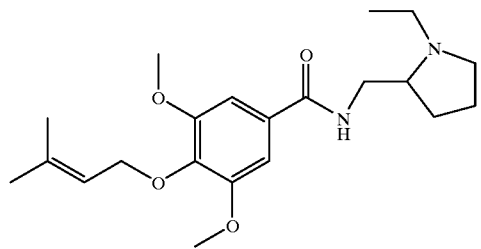
TABLE 2
| Example No. | Anti-ulcer Tests | | Tests for Safety | |
|---|---|---|---|---|
| | WIS | CAP | MTT | AT |
| 15 | 91 | | 2 | |
| 16 | 72 | 99.8 | | 4 |
| 17 | 82 | 100.2 | 22 | |
| 18 | 76 | | 4 | |
| 19 | 89 | | 21 | |
| 20 | 89 | | 23 | |
| 21 | 76 | | | |
TABLE 2-continued
| Example No. | Anti-ulcer Tests | | Tests for Safety | |
|---|---|---|---|---|
| | WIS | CAP | MTT | AT |
| 22 | 80 | | | |
| 23 | 79 | 73.1 | −3 | |
| 24 | 79 | | 12 | |
As clearly from Table 2, even when a lower alkyl group or halogen atom is introduced into the pyrrolidine derivative of compound group 1, a high anti-ulcer effect and acid secretion inhibition effect can be exhibited. Also, it can be understood that they have high safety.

Compound Group 3

A pyrrolidine derivative of this compound group 3 is corresponding to formula 3 mentioned above. As the pyrrolidine derivatives of this compound group 3, the following compounds of Example 25 to 27 were tested.

Example 25:

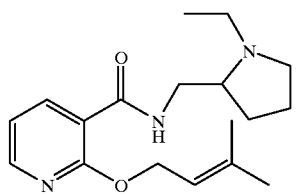

Example 26:

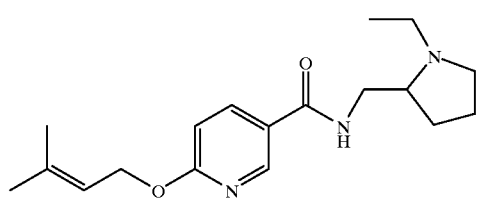

Example 27:

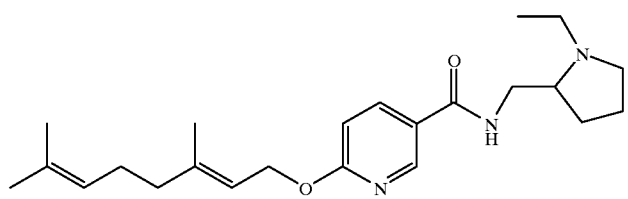

TABLE 3

| Example | Anti-ulcer Test | | Tests for Safety |
|---------|-----------------|-----|------------------|
| No. | WIS | CAP | MTT |
| 25 | 90 | | −15 |
| 26 | 48 | | −8 |
| 27 | 88 | 81.0 | |

As clearly from Table 3, a pyrrolidine derivative of this compound group 3 has a high anti-ulcer effect and acid secretion inhibition effect. Also, it has been shown that they have high safety.

In the following, the manufacturing method of Examples of the present invention will be explained.

At first, the synthetic methods of the material compounds used for synthesizing Examples of the present invention will be shown as Reference Examples 1 to 29.

Reference Example 1

Synthesis of 4-geranyloxybenzoic acid

To a solution of methyl 4-hydroxybenzoate (7.61 g) in acetone(80 ml) were added geranyl bromide (10.9 g) and potassium carbonate (13.8 g), and then the mixture was refluxed with heating for 6 hours. After the reaction, water (150 ml) was added to the reaction mixture, and the mixture was extracted with chloroform. The organic layer was dried over sodium sulfate anhydride and then concentrated under a vacuum. The residue was purified by silica gel column chromatography (hexane:ethyl acetate=9:1), thereby yielding 13.00 g of methyl 4-geranyloxy benzoate.

To a solution of methyl 4-geranyloxybenzoate(13.00 g) in methanol(50 ml) was added aqueous solution(10 ml) of potassium hydroxide (3.90 g). After being stirred overnight at room temperature, the mixture was refluxed with heating for 1 hour. After being acidified with concentrated hydrochloric acid, the reaction mixture was extracted with chloroform. The organic layer was dried over sodium sulfate anhydride and then the solvent was evaporated out under a vacuum. The resulting solid was recrystallized from hexane/ethyl acetate mixed solution, thereby yielding 9.77 g(71%) of the aimed compound.

Reference Example 2

Synthesis of 4-prenyloxybenzoic acid

In a manner identical to Reference Example 1, from methyl 4-hydroxy benzoate (7.61 g) and prenylbromide (7.45 g), 5.86 (57% ) of 4-prenyloxybenzoic acid was obtained.

Reference Example 3

Synthesis of 2-geranyloxybenzoic acid

In a manner identical to Reference Example 1, from methyl 2-hydroxy benzoate(7.61 g) and geranylbromide (10.86 g), 10.23 g(75%) of 2-geranyloxybenzoic acid was obtained.

Reference Example 4

Synthesis of 4-farnesyloxybenzoic acid

In a manner identical to Reference Example 1, from methyl 4-hydroxy benzoate(5.33 g) and farnesylbromide (10.00 g), 7.58 g(63%) of 4-farnesyloxybenzoic acid was obtained.

Reference Example 5
Synthesis of 2-geranylthiobenzoic acid

In a manner identical to Reference Example 1, from methyl 2-mercapto benzoate(8.36 g) and geranylbromide (10.86 g), 10.97 g(76%) of 2-geranylthiobenzoic acid was obtained.

Reference Example 6
Synthesis of 2-geranyloxy-5-methoxybenzoic acid

To a solution of 2-hydroxy-5-methoxybenzoic acid (8.40 g) in ethanol (100 ml) was added sulfuric acid (5 ml) and then the mixture was refluxed with heating for 3 hours. After the reaction, the reaction mixture was concentrated and then water(100 ml) and sodium hydrogencarbonate were added thereto. The mixture was extracted with chloroform and the extract was purified by silica gel column chromatography (hexane:ethyl acetate), thereby yielding ethyl 2-hydroxy-5-methoxybenzoate.

In a manner identical to Reference Example 1, from the resulting compound (9.10 g) and geranylbromide(10.86 g), 7.34 g(48%) of 2-geranyloxy-5-methoxybenzoic acid was obtained.

Reference Example 7
Synthesis of 3,4-diprenyloxybenzoic acid

In a manner identical to Reference Example 1, from ethyl 3,4-dihydroxy benzoate(9.10 g) and prenylbromide(14.90 g), 11.61 g(67%) of 3,4-diprenyloxybenzoic acid was obtained.

Reference Example 8
Synthesis of 3,4-digeranyloxybenzoic acid

In a manner identical to Reference Example 1, from ethyl 3,4-dihydroxy benzoate(9.10 g) and geranylbromide(21.70 g), 13.1 g(62%) of 3,4-digeranyloxybenzoic acid was obtained.

Reference Example 9
Synthesis of 2,4-digeranyloxybenzoic acid

In a manner identical to Reference Example 6, from 2,4-dihydroxybenzoic acid(9.10 g) and geranylbromide (21.70 g), 8.34 g(52%) of 2,4-digeranyloxybenzoic acid was obtained.

Reference Example 10
Synthesis of 3,4-dimethoxy-5-geranyloxybenzoic acid

In a manner identical to Reference Example 1, from methyl 3,4-dimethoxy-5-hydroxybenzoate(7.00 g) and geranylbromide(10.30 g), 5.62 g(51%) of 3,4-dimethoxy-5-geranyloxybenzoic acid was obtained.

Reference Example 11
Synthesis of methyl 3,5-dimethoxy-4-hydroxybenzoate

In a manner identical to Reference Example 6, from syringic acid (17.03 g) and methanol, 13.85 g(76%) of methyl 3,5-dimethoxy-4-hydroxybenzoate was obtained.

Reference Example 12
Synthesis of 3,5-dimethoxy-4-prenyloxybenzoic acid

In a manner identical to Reference Example 1, from methyl 3,5-dimethoxy-4-hydroxybenzoate(7.89 g) and prenylchloride(5.73 g), 5.40 g(55%) of 3,5-dimethoxy-4-prenyloxybenzoic acid was obtained.

Reference Example 13
Synthesis of 3,5-dimethoxy-4-geranyloxybenzoic acid

In a manner identical to Reference Example 1, from methyl 3,5-dimethoxy-4-hydroxybenzoate(5.44 g) and geranylbromide(8.04 g), 5.71 g(67%) of 3,5-dimethoxy-4-geranyloxybenzoic acid was obtained.

Reference Example 14
Synthesis of 4-neryloxybenzoic acid

To a solution of nerol(7.71 g) in dichloromethane(200 ml) were added N-chlorosuccinimide(10.01 g) and dimethylsulfide(6.56 ml) and then the mixture was stirred while being cooled with ice for 4 hours. After the reaction, the reaction mixture was washed with saturated brine and water successively, dried over sodium sulfate anhydride, and concentrated.

In a manner identical to Reference Example 1, from nerylchloride obtained and methyl 4-hydroxybenzoate(7.61 g), 7.47 g(54%) of 4-neryloxybenzoic acid was obtained.

Reference Example 15
Synthesis of 3,4,5-triprenyloxybenzoic acid

In a manner identical to Reference Example 1, from ethyl 3,4,5-trihydroxy benzoate(4.95 g) and prenylbromide(14.90 g), 5.43 g(58%) of 3,4,5-triprenyloxybenzoic acid was obtained.

Reference Example 16
Synthesis of 2-geranyloxy-4-methoxybenzoic acid

In a manner identical to Reference Example 1, from methyl 2-hydroxy-4-methoxybenzoate(9.1 g) and geranylbromide(10.86 g), 7.73 g(51%) of 2-geranyloxy-4-methoxybenzoic acid was obtained.

Reference Example 17
Synthesis of 4-geranyloxy-3-methoxybenzoic acid

In a manner identical to Reference Example 1, from methyl 4-hydroxy-3-methoxybenzoate(9.1 g) and geranylbromide(10.86 g), 7.59 g(63%) of 4-geranyloxy-3-methoxybenzoic acid was obtained.

Reference Example 18
Synthesis of 2-geranyloxy-3-methoxybenzoic acid

In a manner identical to Reference Example 6, from 2-hydroxy-3-methoxybenzoic acid (16.80 g) and geranylbromide (10.86 g), 11.54 g (64%) of 2-geranyloxy-3-methoxybenzoic acid was obtained.

Reference Example 19
Synthesis of 3-geranyloxy-4-methoxybenzoic acid

In a manner identical to Reference Example 1, from methyl 3-hydroxy-4-methoxybenzoate(8.40 g) and geranylbromide(10.36 g), 3.60 g(24%) of 3-geranyloxy-4-methoxybenzoic acid was obtained.

Reference Example 20
Synthesis of 3,5-diprenyloxybenzoic acid

In a manner identical to Reference Example 1, from methyl 3,5-dihydroxy benzoate(8.40 g) and prenylbromide (14.90 g), 10.06 g(69%) of 3,5-diprenyloxybenzoic acid was obtained.

Reference Example 21
Synthesis of 2,4-diprenyloxybenzoic acid

In a manner identical to Reference Example 1, from methyl 2,4-dihydroxy benzoate(8.40 g) and prenylbromide (14.90 g), 8.86 g(61%) of 2,4-diprenyloxybenzoic acid was obtained.

Reference Example 22
Synthesis of 2,5-diprenyloxybenzoic acid

In a manner identical to Reference Example 6, from methyl 2,5-dihydroxy benzoic acid (23.10 g) and prenylbromide (14.90 g), 9.74 g (84%) of 2,5-diprenyloxy benzoic acid was obtained.

Reference Example 23
Synthesis of 3,5-digeranyloxybenzoic acid

In a manner identical to Reference Example 1, from methyl 3,5-dihydroxy benzoate (8.40 g) and geranylbromide (21.72 g), 10.09 g (47%) of 3,5-digeranyloxy benzoic acid was obtained.

Reference Example 24
Synthesis of 2,5-digeranyloxybenzoic acid

In a manner identical to Reference Example 1, from methyl 2,5-dihydroxy benzoate(7.12 g) and geranylbromide (21.72 g), 2.17 g( 10%) of 2,5-digeranyloxybenzoic acid was obtained.

Reference Example 25
Synthesis of 3-fluoro-6-geranyloxybenzoic acid

In a manner identical to Reference Example 6, from 3-fluoro-6-hydroxybenzoic acid(10.00 g) and geranylbromide(10.86 g), 11.57 g(79%) of 3-fluoro-6-geranyloxybenzoic acid was obtained.

Reference Example 26
Synthesis of 3,4-dimethoxy-5-prenyloxybenzoic acid

In a manner identical to Reference Example 6, from 3,4-dimethoxy-5-hydroxybenzoic acid and methanol, methyl 3,4-dimethoxy-5-hydroxybenzoate was obtained.

In a manner identical to Reference Example 1, from Methyl 3,4-dimethoxy-5-hydroxybenzoate and prenylchloride, 3,4-dimethoxy-5-prenyloxybenzoic acid was obtained.

Reference Example 27
Synthesis of 6-prenyloxynicotinic acid

In a manner identical to Reference Example 1, from 6-hydroxynicotinic acid(6 g) and prenylbromide(13.5 g), prenyl 6-prenyloxynicotinate was obtained.

In a manner identical to Reference Example 1, the resulting compound was hydrolyzed, thereby yielding 3.59 g of 6-prenyloxynicotinic acid.

Reference Example 28
Synthesis of 2-prenyloxynicotinic acid

In a manner identical to Reference Example 1, from 2-hydroxynicotinic acid and prenylbromide, prenyl 2-prenyloxynicotinate was obtained.

In a manner identical to Reference Example 1, the resulting compound was hydrolyzed, thereby yielding 2-prenyloxynicotinic acid.

Reference Example 29
Synthesis of 6-geranyloxynicotinic acid

In a manner identical to Reference Example 1, from 6-hydroxynicotinic acid and geranylbromide, geranyl 6-geranyloxynicotinate was obtained.

In a manner identical to Reference Example 1, the resulting compound was hydrolyzed, thereby yielding 3.59 g of 6-geranyloxynicotinic acid.

EXAMPLE 1
1-ethyl-2-(4-geranyloxybenzoylaminomethyl)pyrrolidine

In a manner identical to Example 15, 4-geranyloxybenzoic acid(1.45 g) was subjected to a condensation reaction with 2-aminomethyl-1-ethylpyrrolidine (0.7 ml), thereby yielding 1.96 g(98%) of the aimed compound.

$^1$H-NMR (CDCl$_3$) δ: 7.73(2H, d, J=8.8 Hz), 6.95(1H, bs), 6.91(2H, d, J=8.8 Hz), 5.47(1H, t, J=6.8 Hz), 5.13-5.05(1H, m), 4.57(2H, d, J=6.4 Hz), 3.28-3.13(1H, m), 2.95-2.81(1H, m), 2.16-2.54(1H, m), 2.33-2.22(1H, m), 2.20-2.00(4H, m), 1.98-1.86(1H, m), 1.74(3H, s), 1.71(3H, s), 1.67(3H, s), 1.12(3H, t, J=7.3 Hz).

EXAMPLE 2
1-ethyl-2-(2-geranyloxybenzoylaminomethyl)pyrrolidine

In a manner identical to Example 15, 2-geranyloxybenzoic acid(1.37 g) was subjected to a condensation reaction with 2-aminomethyl-1-ethylpyrrolidine (0.7 ml), thereby yielding 1.53 g(80%) of the aimed compound.

$^1$H-NMR (CDCl$_3$) δ: 8.34(1H, bs), 8.21(1H, dd, J=2.0 Hz, 7.8 Hz), 7.40(1H, dt, J=2.0 Hz, 8.3 Hz), 7.05(1H, t, J=7.8 Hz), 6.94(1H, d, J=8.3 Hz), 5.50(1H, t, J=6.4 Hz), 5.11-5.02 (1H, m), 4.72(2H, d, J=6.4 Hz), 3.28-3.13(1H, m), 2.95-2.81(1H, m), 2.16-2.54(1H, m), 2.33-2.22(1H, m), 2.20-2.00 (4H, m), 1.98-1.86(1H, m), 1.74(3H, s), 1.71(3H, s), 1.67 (3H, s), 1.12(3H, t, J=7.3 Hz).

EXAMPLE 3
1-ethyl-2-(4-prenyloxybenzoylaminomethyl)pyrrolidine

In a manner identical to Example 15, 4-prenyloxybenzoic acid(1.44 g) was subjected to a condensation reaction with 2-aminomethyl-1-ethylpyrrolidine (1.0 ml), thereby yielding 1.02 g(46%) of the aimed compound.

$^1$H-NMR (CDCl$_3$) δ: 7.76(2H, d, J=8.8 Hz), 6.97(1H, bs), 6.92(2H, d, J=8.8 Hz), 5.54-5.44(1H, m), 4.55(2H, d, J=6.4 Hz), 3.69-3.64(1H, m), 3.38-3.22(2H, m), 2.90-2.70(2H, m), 2.37-2.19(2H, m),1.97-1.87(1H, m), 1.80(3H, s), 1.75(3H, s), 1.69-1.63(3H, m), 1.14(3H, t, J=6.8 Hz).

EXAMPLE 4
1-ethyl-2-(4-neryloxybenzoylaminomethyl)pyrrolidine

In a manner identical to Example 15, 4-neryloxybenzoic acid(1.64 g) was subjected to a condensation reaction with 2-aminomethyl-1-ethylpyrrolidine (0.84 ml), thereby yielding 0.69 g(30%) of the aimed compound.

$^1$H-NMR (CDCl$_3$) δ: 7.75(2H, d, J-=8.8 Hz), 6.29(2H, d, J=8.8 Hz), 6.83(1H, bs), 5.50(1H, t, J=6.8 Hz), 5.11(1H, t, J=5.8 Hz), 4.54(2H, d, J=6.8 Hz), 3.74-3.66(1H, m), 3.38-3.20(2H, m), 2.92-2.70(2H, m), 2.19-2.09(4H, m), 1.97-1.87 (1H, m), 1.80(3H, s), 1.68(3H, s), 1.60(3H, s), 1.14(3H, t, J=6.8 Hz).

EXAMPLE 5
1-ethyl-2-(2,4-diprenyloxybenzoylaminomethyl)pyrrolidine

In a manner identical to Example 15, 2,4-diptenyloxybenzoic acid(1.45 g) was subjected to a condensation reaction with 2-aminomethyl-1-ethylpyrrolidine (0.7 ml), thereby yielding 1.96 g(98%) of the aimed compound.
$^1$H-NMR (CDCl$_3$) δ: 8.19-8.15(2H, m), 6.59(1H, d, J=2.4 Hz), 6.49(1H, d, J=2.2 Hz), 5.52-5.48(2H, m), 4.63(2H, d, J=5.9 Hz), 4.54(2H, d, J=6.3 Hz), 3.28-3.13(1H, m), 2.95-2.81(1H, m), 2.16-2.54(1H, m), 2.33-2.22(1H, m), 2.20-2.00 (4H, m), 1.98-1.86(1H, m), 1.80(6H, s), 1.75(6h, s), 1.12 (3H, t, J=7.3 Hz).

EXAMPLE 6

1-ethyl-2-(2,5-diprenyloxybenzoylaminomethyl)pyrrolidine

In a manner identical to Example 15, 2,5-diprenyloxybenzoic acid(1.45 g) was subjected to a condensation reaction with 2-aminomethyl-1-ethylpyrrolidine (0.7 ml), thereby yielding 1.40 g(70%) of the aimed compound.
$^1$H-NMR (CDCl$_3$) δ: 8.44(1H, bs), 7.77(1H, d, J=3.4 Hz), 6.98(1H, dd, J=3.4 Hz, 8.8 Hz), 6.90(1H, d, J=8.8 Hz), 5.52-4.94(2H, m), 4.63(2H, d, J=6.4 Hz), 4.52(2H, d, J=6.4 Hz), 3.28-3.13(1H, m), 2.95-2.81(1H, m), 2.16-2.54(1H, m), 2.33-2.22(1H, m), 2.20-2.00(4H,m), 1.98-1.86(1H, m), 1.79 (6H, s), 1.74(6H, s), 1.12(3H, t, J=7.3 Hz).

EXAMPLE 7

1-ethyl-2-(3,4-diprenyloxybenzoylaminomethyl)pyrrolidine

In a manner identical to Example 15, 3,4-diprenyloxybenzoic acid(1.45 g) was subjected to a condensation reaction with 2-aminomethyl-1-ethylpyrrolidine (0.7 ml), thereby yielding 1.09 g(55%) of the aimed compound. m.p. 80.0–81.5° C.

$^1$H-NMR (CDCl$_3$) δ: 7.44(1H, s), 6.86(1H, d, J=8.0 Hz), 5.50-5.45(1H, m), 4.64(4H, d, J=6.8 Hz), 3.27-3.14(1H, m), 2.95-2.81(1H, m), 2.15-2.55(1H, m), 2.32-2.23(1H, m), 2.20-1.98(4H,m), 1.96-1.84(1H, m), 1.74(3H, s), 1.71(3H, s), 1.67(6H, s), 1.12(3H, t, J=7.3 Hz).

EXAMPLE 8

1-ethyl-2-(3,5-diprenyloxybenzoylaminomethyl)pyrrolidine

In a manner identical to Example 15, 3,5-diprenyloxybenzoic acid(1.45 g) was subjected to a condensation reaction with 2-aminomethyl-1-ethylpyrrolidine (0.7 ml), thereby yielding 0.78 g(39%) of the aimed compound.
$^1$H-NMR (CDCl$_3$) δ: 6.94(2H, d, J=2.4 Hz), 6.61(1H, t, J=2.4 Hz), 5.49(1H, t, J=5.4 Hz), 4.51(4H, d, J=6.8 Hz), 3.28-3.13(1H, m), 2.95-2.81(1H, m), 2.16-2.54(1H, m), 2.33-2.22(1H, m), 2.20-2.00(4H,m), 1.98-1.86(1H, m), 1.79 (6H, s), 1.74(6H, s), 1.12(3H, t, J=7.3 Hz).

EXAMPLE 9

1-ethyl-2-(2,4-digeranyloxybenzoylaminomethyl)pyrrolidine

In a manner identical to Example 15, 2,4-digeranyloxybenzoic acid(2.13 g) was subjected to a condensation reaction with 2-aminomethyl-1-ethylpyrrolidine (0.7 ml), thereby yielding 2.03 g(76%) of the aimed compound.
$^1$H-NMR (CDCl$_3$) δ: 8.20(1H, bs), 8.15(1H, d, J=8.8 Hz), 6.58(1H, dd, J=2.0 Hz, 6.8 Hz), 6.49(1H, d, J=2.0 Hz), 5.52-5.46(2H, m), 5.09-5.07(2H, m), 4.67(2H, d, J=6.4 Hz), 4.56(2H, d, J=6.4 Hz), 3.28-3.13(1H, m), 2.95-2.81(1H, m), 2.16-2.54(1H, m), 2.33-2.22(1H, m), 2.20-2.00(8H,m), 1.98-1.86(1H, m), 1.74(6H, s), 1.68-1.67(6H, s), 1.12(3H, t, J=7.3 Hz).

EXAMPLE 10

1-ethyl-2-(2,5-digeranyloxybenzoylaminomethyl)pyrrolidine

In a manner identical to Example 15, 2,5-digeranyloxybenzoic acid(2.13 g) was subjected to a condensation reaction with 2-aminomethyl-1-ethylpyrrolidine (0.7 ml), thereby yielding 1.47 g(55%) of the aimed compound.
$^1$H-NMR (CDCl$_3$) δ: 8.44(1H, bs), 7.77(1H, d, J=3.4 Hz), 6.98(1H, dd, J=3.4 Hz, 8.8 Hz), 6.90(1H, d, J=8.8 Hz), 5.53-5.42(2H, m), 5.11-5.02(2H, m), 4.63(2H, d, J=6.4 Hz), 4.52(2H, d, J=6.4 Hz), 3.28-3.13(1H, m), 2.95-2.81(1H, m), 2.16-2.54(1H, m), 2.33-2.22(1H, m), 2.20-2.00(4H,m), 1.98-1.86(1H, m), 1.72(6H, s), 1.67(6H, s), 1.60(6H, s), 1.12(3H, t, J=7.3 Hz).

EXAMPLE 11

1-ethyl-2-(3,4-digeranyloxybenzoylaminomethyl)pyrrolidine

In a manner identical to Example 15, 3,4-digeranyloxybenzoic acid(2.13 g) was subjected to a condensation reaction with 2-aminomethyl-1-ethylpyrrolidine (0.7 ml), thereby yielding 1.93 g(72%) of the aimed compound.
$^1$H-NMR (CDCl$_3$)δ: 8.46(1H, bs), 7.76(1H, d, J=3.0 Hz), 7.06-6.82(2H, m), 5.50-5.45(2H, m), 5.08-5.02(2H, m), 4.64 (4H, d, J=6.8 Hz), 3.27-3.14(1H, m), 2.95-2.81(1H, m), 2.15-2.55(1H, m), 2.32-2.23(1H, m), 2.20-1.98(4H,m), 1.96-1.84(1H, m), 1.74(3H, s), 1.71(3H, s), 1.67(6H, s), 1.59(6H, s), 1.12(3H, t, J=7.3 Hz).

EXAMPLE 12

1-ethyl-2-(3,5-digeranyloxybenzoylaminomethyl)pyrrolidine

In a manner identical to Example 15, 3,5-digeranyloxybenzoic acid(2.13 g) was subjected to a condensation reaction with 2-aminomethyl-1-ethylpyrrolidine (0.7 ml), thereby yielding 2.14 g(82%) of the aimed compound.
$^1$H-NMR (CDCl$_3$) δ: 6.94(2H, d, J=2.4 Hz), 6.61(1H, d, J=2.4 Hz), 5.49(2H, t, J=5.4 Hz), 5.12-5.04(2H, m), 4.51 (4H, d, J=6.8 Hz), 3.28-3.13(1H, m), 2.95-2.81(1H, m), 2.16-2.54(1H, m), 2.33-2.22(1H, m), 2.20-2.00(4H,m), 1.98-1.86(1H, m), 1.73(6H, s), 1.68(6H, s), 1.60(6H, s), 1.12(3H, t, J=7.3 Hz).

EXAMPLE 13

1-ethyl-2-(3,4,5-triprenyloxybenzoylaminomethyl)pyrrolidine

In a manner identical to Example 15, 3,4,5-triprenyloxybenzoic acid(0.94 g) was subjected to a condensation reaction with 2-aminomethyl-1-ethylpyrrolidine (0.35 g), thereby yielding 1.21 g(79%) of the aimed compound.
$^1$H-NMR (CDCl$_3$) δ: 7.01(2H, s), 6.73(1H, s), 5.58-5.47(3H, m), 4.59(4H, d, J=5.9 Hz), 4.54(2H, d, J=6.8 Hz), 3.71-3.63 (1H, m), 3.34-3.25(1H, m), 3.24-3.16(1H, m), 2.90-2.76(1H, m), 2.75-2.65(1H, m), 2.32-2.18(2H, m), 1.95-1.85(1H, m), 1.77(6H, s), 1.73(9H, s), 1.66(3H, s), 1.12(3H, t, J=7.8 Hz).

EXAMPLE 14

1-ethyl-2-(2-geranylthiobenzoylaminomethyl)pyrrolidine

In a manner identical to Example 15, 2-geranylthiobenzoic acid(2.03 g) was subjected to a condensation reaction with 2-aminomethyl-1-ethylpyrrolidine (1.0 ml), thereby yielding 1.52 g(54%) of the aimed compound.

¹H-NMR (CDCl₃) δ: 7.63(1H, d, J=7.8 Hz), 7.48(1H, bs), 7.38-7.19(3H, m), 5.28(1H, t, J=7.8 Hz), 5.05(1H, t, J=6.4 Hz), 4.72(2H, d, J=6.4 Hz), 3.80-3.74(1H, m), 3.54(2H, d, J=7.8 Hz), 3.47-3.29(2H, m), 3.00-2.90(1H, m), 2.40-2.26 (2H, m), 2.10-1.95(4H, m), 1.84-1.69(4H, m), 1.66(3H, s), 1.59(3H, s), 1.14(3H, t, J=6.8 Hz).

EXAMPLE 15

1-ethyl-2-(3-geranyloxy-4-methoxybenzoylaminomethyl) pyrrolidine 3-geranyloxy-4-methoxybenzoic acid(1.52 g) was dissolved in chloroform (50 ml) and triethylamine (1.4 ml), and then diphenylphosphinic chloride(1.0 ml) was added thereto while being cooled with ice. After being stirred for 15 minutes, the mixture, with 2-aminomethyl-1-ethylpyrrolidine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.47 g(71%) of the aimed compound.
¹H-NMR (CDCl₃) δ: 7.45(1H, d, J=2.0 Hz), 6.88(1H, d, J=8.3 Hz), 6.66(1H, bs), 5.53(1H, t, J=6.4 Hz), 5.09(1H, t, J=6.4 Hz), 4.67(2H, d, J=6.4 Hz), 3.91(3H, s), 3.28-3.13(1H, m), 2.95-2.81(1H, m), 2.16-2.54(1H, m), 2.33-2.22(1H, m), 2.20-2.00(4H,m), 1.98-1.86(1H, m), 1.74(3H, s), 1.71(3H, s), 1.67(3H, s), 1.12(3H, t, J=7.3 Hz).

EXAMPLE 16

1-ethyl-2-(4-geranyloxy-3-methoxybenzoylaminomethyl) pyrrolidine

In a manner identical to Example 15, 4-geranyloxy-3-methoxybenzoic acid(1.52 g) was subjected to a condensation reaction with 2-aminomethyl-1-ethylpyrrolidine (0.7 ml), thereby yielding 1.63 g(79%) of the aimed compound.
¹H-NMR (CDCl₃) δ: 7.45(1H, d, J=2.0 Hz), 7.28(1H, dd, J=2.0 Hz, 8.3 Hz), 6.85(1H, d, J=8.3 Hz), 7.09(1H, bs), 5.50(1H, t, J=6.4 Hz), 5.06(1H, t, J=6.8 Hz), 4.65(2H, d, J=6.4 Hz), 3.91(3H, s), 3.28-3.13(1H, m), 2.95-2.81(1H, m), 2.16-2.54(1H, m), 2.33-2.22(1H, m), 2.20-2.00(4H,m), 1.98-1.86(1H, m), 1.74(3H, s), 1.71(3H, s), 1.67(3H, s), 1.12(3H, t, J=7.3 Hz).

EXAMPLE 17

1-ethyl-2-(2-geranyloxy-3-methoxybenzoylaminomethyl) pyrrolidine

In a manner identical to Example 15, 2-geranyloxy-3-methoxybenzoic acid(1.52 g) was subjected to a condensation reaction with 2-aminomethyl-1-ethylpyrrolidine (0.7 ml), thereby yielding 1.84 g(89%) of the aimed compound.
¹H-NMR (CDCl₃) δ: 8.38(1H, bs), 7.70(1H, dd, J=2.0 Hz, 7.8 Hz), 7.12(1H, dt, J=2.0 Hz, 7.8 Hz), 7.00(1H, d, J=8.3 Hz), 5.53(1H, t, J=7.3 Hz), 5.07-5.02(1H, m), 4.64(2H, d, J=7.3 Hz), 3.91(3H, s), 3.28-3.13(1H, m), 2.95-2.81(1H, m), 2.16-2.54(1H, m), 2.33-2.22(1H, m), 2.20-2.00(4H,m), 1.98-1.86(1H, m), 1.74(3H, s), 1.71(3H, s), 1.67(3H, s), 1.12(3H, t, J=7.3 Hz).

EXAMPLE 18

1-ethyl-2-(2-geranyloxy-4-methoxybenzoylaminomethyl) pyrrolidine

In a manner identical to Example 15, 2-geranyloxy-4-methoxybenzoic acid(1.52 g) was subjected to a condensation reaction with 2-aminomethyl-1-ethylpyrrolidine (0.7 ml), thereby yielding 1.43 g(69%) of the aimed compound.
¹H-NMR (CDCl₃) δ: 8.24(1H, bs), 8.19(1H, d, J=8.8 Hz), 6.57(1H, dd, J=2.0 Hz, 8.8 Hz), 6.47(1H, d, J=2.4 Hz), 5.55-5.46(1H, m), 5.10-5.02(1H, m), 4.67(2H, d, J=6.4 Hz), 3.83(3H, s), 3.28-3.13(1H, m), 2.95-2.81(1H, m), 2.16-2.54 (1H, m), 2.33-2.22(1H, m), 2.20-2.00(4H,m), 1.98-1.86(1H, m), 1.74(3H, s), 1.71(3H, s), 1.67(3H, s), 1.12(3H, t, J=7.3 Hz).

EXAMPLE 19

1-ethyl-2-(2-geranyloxy-5-methoxybenzoylaminomethyl) pyrrolidine

In a manner identical to Example 15, 2-geranyloxy-5-methoxybenzoic acid(1.52 g) was subjected to a condensation reaction with 2-aminomethyl-1-ethylpyrrolidine (0.7 ml), thereby yielding 1.78 g(86%) of the aimed compound.
¹H-NMR (CDCl₃) δ: 8.46(1H, bs), 7.76(1H, dd, J=3.0 Hz), 7.06-6.82(2H, m), 5.50-5.45(1H, m), 5.08-5.02(1H, m), 4.64 (2H, d, J=6.8 Hz), 3.82(3H, s), 3.28-3.13(1H, m), 2.95-2.81 (1H, m), 2.16-2.54(1H, m), 2.33-2.22(1H, m), 2.20-2.00(4H, m), 1.98-1.86(1H, m), 1.74(3H, s), 1.71(3H, s), 1.67(3H, s), 1.12(3H, t, J=7.3 Hz).

EXAMPLE 20

1-ethyl-2-(3-fluoro-6-geranyloxybenzoylaminomethyl) pyrrolidine

In a manner identical to Example 15, 3-fluoro-6-geranyloxybenzoic acid(1.46 g) was subjected to a condensation reaction with 2-aminomethyl-1-ethylpyrrolidine (0.7 ml), thereby yielding 1.68 g(84%) of the aimed compound.
¹H-NMR (CDCl₃) δ: 8.38(1H, bs), 7.91(1H, d, J=9.8 Hz), 7.00-7.10(1H, m), 6.90-6.83(1H, m), 5.52-5.42(1H, m), 5.00-5.07(1H, m), 4.70(2H, d, J=6.4 Hz), 3.72-3.82(1H, m), 3.30-3.12(2H, m), 2.94-2.80(1H, m), 2.65-2.54(1H, m), 2.30-1.55(10H, m), 1.74(3H, s), 1.66(13H, s), 1.59(3H, s), 1.11(3H, t, J=6.8 Hz).

EXAMPLE 21

1-ethyl-2-(3,5-dimethoxy-4-geranyloxybenzoylaminomethyl)pyrrolidine

In a manner identical to Example 15, 3,5-dimethoxy-4-geranyloxy benzoic acid (0.80 g) was subjected to a condensation reaction with 2-aminomethyl-1-ethylpyrrolidine (0.31 g), thereby yielding 1.02 g(95%) of the aimed compound.

EXAMPLE 22

1-ethyl-2-(3,4-dimethoxy-5-geranyloxybenzoylaminomethyl)pyrrolidine

In a manner identical to Example 15, 3,4-dimethoxy-5-geranyloxy benzoic acid (0.80 g) was subjected to a condensation reaction with 2-aminomethyl-1-ethylpyrrolidine (0.31 g), thereby yielding 0.62 g(58%) of the aimed compound.
¹H-NMR (CDCl₃) δ: 7.03(1H, s), 7.02(1H, s), 6.78(1H, s), 5.55-5.48(1H, m), 5.11-5.04(1H, m), 4.63(2H, d, J=6.4 Hz), 3.90(3H, s), 3.88(3H, s), 3.69-3.63(1H, m), 3.32-3.29(1H, m), 3.24-3.15(1H, m), 2.87-2.82(1H, m), 2.78-2.67(H, m), 2.32-2.20(2H, m), 2.12-2.07(4H, m), 1.95-1.87(2H, m), 1.74-1.70(5H, s), 1.66(3H, s), 1.59(3H, s), 1.13(3H, t, J=6.8 Hz).

EXAMPLE 23

1-ethyl-2-(3,4-dimethoxy-5-prenyloxybenzoylaminomethyl)pyrrolidine

In a manner identical to Example 15, 3,4-dimethoxy-5-prenyloxybenzoic acid (0.80 g) was subjected to a condensation reaction with 2-aminomethyl-1-ethylpyrrolidine (0.39 g), thereby yielding 1.78 g(69%) of the aimed compound.
¹H-NMR (CDCl₃) δ: 7.07(2H, S), 7.06(f H, s), 5.56 -5.49 (0H , m), 4.62(2H, d, J=6.3 Hz), 3.91(3H, ), 3.89(3H, 7), 3.72-3.66(3H, m), 3.38-3.34(9 H, m), 3.31-3.20(8H, m), 2.93-2.81(2H, m), 2.36-2.28(2H, m9), 1.98-1.81(2H, m), 1.78(3H, s), 1.75(3H, s), 1.71-1.63(2H, m), 1.16(3H, t, J=7.3 Hz).

EXAMPLE 24
1-ethyl-2-(3,5-dimethoxy-4-prenyloxybenzoylaminomethyl)pyrrolidine In a manner identical to Example 15, 3,5-dimethoxy-4-prenyloxybenzoic acid (0.80 g) was subjected to a condensation reaction with 2-aminomethyl-1-ethylpyrrolidine (0.39 g), thereby yielding 1.01 g(89%) of the aimed compound.
¹H-NMR (CDCl₃) δ: 7.05(21H, s), 5.60-5.51(4 H, m), 4.55(21, d, J=7.3 Hz), 3.90(6H, s), 3.71-3.64(3H , m), 3.37-3.34(H1, m7), 3.30-3.21(H, , m), 2.92-2.84(1H, 3), 2.83-2.75(11H, m), 2.35-2.28(2H , m), 2.00-1.91((H , m), 1.82-1.76((H, m), 1.75(3H, s),1.67(3H, s), 1.16(3H, t, J=7.3 Hz).

EXAMPLE 25
1-ethyl-2-(2-prenyloxynicotinoylaminomethyl)pyrrolidine

In a manner identical to Example 15, 2-prenyloxynicotinic acid (1.00 g) was subjected to a condensation reaction with 2-aminomethyl-1-ethylpyrrolidine (0.63 g), thereby yielding 1.41 g(92%) of the aimed compound.
¹H-NMR (CDCl₃) δ: 9.92(1H, s), 8.53-8.47(1H, m), 7.55-7.48(1H, m), 6.41-6.34(1H, m), 5.35-5.29(1H, m), 4.70-4.52 (2H, m), 3.78-3.71(1H, m), 3.32-3.21(2H, m), 2.99-2.91(1H, m), 2.80-2.60(1H, m), 2.33(2.41(1H, m), 2.27-2.21( 1H, m), 2.02-1.92(1H, m), 1.89-1.63(9H, m), 1.16(3H, t, J-=7.3 Hz).

EXAMPLE 26
1-ethyl-2-(6-prenyloxynicotinoylaminomethyl)pyrrolidine

In a manner identical to Example 15, 6-prenyloxynicotinic acid (0.70 g) was subjected to a condensation reaction with 2-aminomethyl-1-ethylpyrrolidine (0.90 g), thereby yielding 0.73 g(68%) of the aimed compound.
¹H-NMR (CDCl₃) δ: 8.09(1H, d, J=2.9 Hz), 7.58-7.50(1H, m), 6.72(1H, s), 6.54(1H, d, J=9.8 Hz), 5.35-5.28(1H, m), 4.57(2H, d, J=7.3 Hz), 3.67-3.01(1H, m), 3.29-3.19(2H, m), 2.75-2.67(1H, m), 2.33-2.20(2H, m), 1.79(6H, s), 1.76-1.67 (1H, m), 1.66-1.55(1H, m), 1.13(3H, t, J=7.3 Hz).

EXAMPLE 27
1-ethyl-2-(6-gearnyloxynicotinoylaminomethyl)pyrrolidine

In a manner identical to Example 15, 6-geranyloxynicotinic acid (0.75 g) was subjected to a condensation reaction with 2-aminomethyl-1-ethylpyrrolidine (0.36 g), thereby yielding 0.95 g(90%,) of the aimed compound.
¹H-NMR (CDCl₃)δ: 8.12(1H, d, J=2.4 Hz), 7.61-7.52(1H, m), 6.87(1H, s), 6.55(1H, d, J=9.3 Hz), 5.35-5.27(1H, m), 5.10-5.01(1H, m), 4.60(2H, d, J=6.8 Hz), 3.68-3.62(1H, m), 3.32-3.26(2H, m), 2.88-f(2H, m), 2.35-2.20(2H, m), 2.13-2.02(4H, m), 1.98-1.81(1H, m), 1.79-1.70(6H, m), 1.66(3H, s), 1.59(3H, s), 1.15(3H, t, J=6.8 Hz).

EXAMPLE 28
1-ethyl-2-(4-farnesyloxybenzoylaminomethyl)pyrrolidine

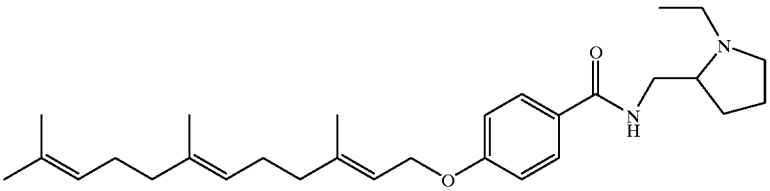

In a manner identical to Example 15, 4-farnesyloxybenzoic acid (1.71 g) was subjected to a condensation reaction with 2-aminomethyl-1-ethylpyrrolidine (0.7 ml), thereby yielding 1.73 g(77%) of the aimed compound.
¹H-NMR (CDCl₃) δ: 7.74(2H, d, J=8.3 Hz), 6.93(2H, d, J=8.8 Hz), 6.83( 1H, bs), 5.48(1H, t, J-5.4 Hz), 5.14-5.07 (2H, m), 4.57(2H, d, J=6.4 Hz), 3.75-3.65(1H, m), 3.32-3.19(2H, m), 2.89-2.80(1H, m), 2.70(1H, bs), 2.33-1.88 (12H, m), 1.74(3H, s), 1.67( 3H, s), 1.60(6H, s), 1.12(31H, t, J=7.3 Hz).

What is claimed is:
1. A pyrrolidine derivative or a salt thereof expressed by the following formula 1:

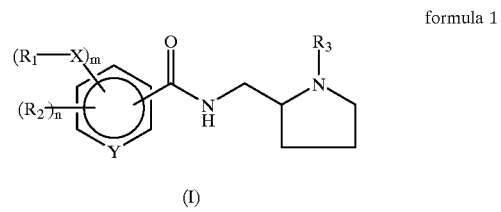

formula 1

(I)

wherein R₁ is an alkenyl group;
R₂ is a lower alkoxy group or a halogen atom;
R₃ is a lower alkyl group;
X is a group expressed by —O— or —S—;
Y is nitrogen atom;
m is an integer of 1 to 3; and
n is an integer of 0 to 2.
2. A pyrrolidine derivative or a salt thereof according to claim 1, wherein n is 0.
3. A pyrrolidine derivative or a salt thereof according to claim 1, wherein n is 1 or 2.
4. A pyrrolidine derivative or a salt thereof according to claim 3, wherein m is 1.
5. A pyrrolidine derivative or a salt thereof according to claim 1, wherein X is —O—.
6. A pyrrolidine derivative or a salt thereof according to claim 1, which expressed by the following formula 3:

formula 3

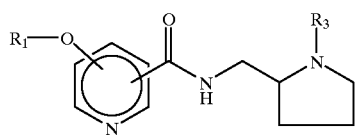

wherein $R_1$ and $R_3$ are same as those in the above-mentioned formula 1.

7. A pyrrolidine derivative or a salt thereof according to claim 1, wherein $R_1$ is prenyl, geranyl, neryl or farnesyl group.

8. A pyrrolidine derivative or a salt thereof according to claim 1, wherein $R_3$ is ethyl group.

9. An anti-ulcer drug comprising, as an effective ingredient, a pyrrolidine derivative or a pharmacologically acceptable salt thereof according to claim 1, together with a pharmaceutically acceptable carrier.

10. An antibacterial drug against *Helicobacter pyroli* comprising, as an effective ingradient, a pyrrolidine derivative or pharmaceutically acceptable salt thereof according to claim 1, together with a pharmaceutically acceptable carrier.

11. A method for the treatment of peptic ulcers in man or mammals, which comprises administering an effective amount of a pyrrolidine derivative or a pharmacologically acceptable salt thereof according to claim 1 to man or mammals.

12. A method according to claim 11, wherein said peptic ulcers are gastric ulcers in man.

13. A method for the inhibition of acid secretion in stomach of man or mammals, which comprises administering an effective amount of a pyrrolidine derivative or a pharmacologically acceptable salt thereof according to claim 1 to man or mammals.

14. A method for the inhibition of growth of *Helicobacter pyroli* in stomach of man or mammals, which comprises administering an effective amount of a pyrrolidine derivative or a pharmacologically acceptable salt thereof according to claim 1 to man or mammals.

15. A method for the prevention of peptic ulcers in man or mammals, which comprises administering an effective amount of a pyrrolidine derivative or a pharmacologically acceptable salt thereof according to claim 1 to man or mammals.

16. A method according to claim 15, wherein said peptic ulcers are gastric ulcers in man.

* * * * *